| United States Patent [19] | [11] | 4,349,529 |
|---|---|---|
| Morcos et al. | [45] | Sep. 14, 1982 |

[54] DIAGNOSTIC AND THERAPEUTIC CAPSULES AND METHOD OF PRODUCING

[75] Inventors: Nabil A. Morcos, South Brunswick; Thomas A. Haney, East Brunswick; Paul W. Wedeking, Cranbury, all of N.J.

[73] Assignee: E. R. Squibb & Sons, Inc., Princeton, N.J.

[21] Appl. No.: 140,341

[22] Filed: Apr. 14, 1980

[51] Int. Cl.³ .................. A61K 43/00; A61K 49/00; G01T 1/00
[52] U.S. Cl. .................................. 424/1; 128/659; 424/21; 424/37; 427/5
[58] Field of Search .............. 424/1, 1.5, 9, 19, 21, 424/35, 37, 38; 427/5; 128/1.1 G, 1.2, 659

[56] References Cited

U.S. PATENT DOCUMENTS

| 1,683,466 | 5/1927 | Horigan | 424/21 |
| 2,911,338 | 11/1959 | Tabern et al. | 424/1 X |
| 3,780,170 | 12/1973 | Goodhart et al. | 424/35 |
| 4,235,871 | 11/1980 | Papahadjopoulos et al. | 424/19 |

FOREIGN PATENT DOCUMENTS 7210728  2/1973  Netherlands ............................ 424/1

*Primary Examiner*—Christine M. Nucker
*Attorney, Agent, or Firm*—Lawrence S. Levinson; Donald J. Barrack

[57] ABSTRACT

An article of manufacture comprising a pharmaceutical radioactive capsule formed essentially of a non-toxic, water soluble material adapted to being ingested and rapidly disintegrating on contact with fluids of the gastro-intestinal tract, and having a filler material supporting a pharmaceutically useful radioactive compound absorbable from the gastro-intestinal tract said filler material being supported by said capsule. And a method of filling a pharmaceutical radioactive capsule comprising providing filler material supporting a pharmaceutically useful radioactive compound and transporting said filler material carrying a pharmaceutically useful radioactive compound into the chamber of said capsule.

10 Claims, No Drawings

DIAGNOSTIC AND THERAPEUTIC CAPSULES AND METHOD OF PRODUCING

BACKGROUND OF THE INVENTION

The present invention relates to a new diagnostic and therapeutic form of radioactive compounds and more particularly to an improved encapsuled form of diagnostically and therapeutically useful radioactive compounds.

Radioactive compounds, such as sodium radioactive iodide (I-131), have been dispensed by measuring out, usually by remote control suitable volumes of a radioactive compound in an aqueous medium. For diagnostic uses in particular, most of the radioactive material is given orally and for such use it was customary to measure or pipette the aqueous solution of the radioactive compound into a cup or glass immediately prior to administering orally to the patient. The foregoing method of administering radioactive materials resulted in serious contamination of glassware and other equipment as well as the mouth and esophagus of the patient.

The foregoing disadvantages were in part overcome by adding an aqueous solution of a radioactive compound to a gelatin capsule which is filled with sodium phosphate, the latter serving to remove part or all of the water to form a hydrate with the result that the radioactive material is disposed on a fine, fluffy powder confined within the interior of the said capsule. Experience showed that the latter capsules were not well suited for this purpose because the action of the water on the gelatin capsules during filling causes the development of irregular areas in the capsules. Moreover, when the capsules are damaged or broken, the remaining capsules and adjacent container becomes seriously radioactively contaminated. The latter contamination is even more serious if the breakage of the capsules occurs during the handling of the capsules while being given to the patient.

Tabern et al. U.S. Pat. No. 2,911,338 discloses providing a gelatin capsule or capsule of other thermoplastic, water soluble, non-toxic material which has disposed interiorally as an integral part thereof or adsorbed on the interior wall a therapeutic or diagnostic dose of an organic or inorganic radioactive compound, such as sodium radioactive iodide. Tabern discloses that it is possible to provide a capsule composed of a non-toxic therapeutic water soluble material having interiorally disposed as an integral part thereof a therapeutic or diagnostic dose of a radioactive compound by forming a solution of the said radioactive compound in a relatively volatile essentially non-aqueous organic solvent, depositing a carefully measured volume of the said solution in an empty capsule or half thereof, and completely removing the solvent to leave the radioactive compound adsorbed on the inner walls of the capsule as a firmly attached integral part thereof.

The present invention provides a pharmaceutical radioactive capsule of improved shelf life.

DETAILED DESCRIPTION OF THE INVENTION

The pharmaceutical radioactive capsule of the present invention is formed of a nontoxic water soluble material adapted to be ingested and rapidly disintegrating on contact with fluids of the gastro-intestinal tract. Each capsule is provided with filler material supporting a pharmaceutically useful radioactive compound absorbable from the gastro-intestinal tract. The filler material is supported by the capsule.

The filler material preferably is polyethylene glycol. Most preferably the polyethylene glycol is Carbowax 1000 to 4000. The radioactive compound is preferably iodine i.e. I-131 or I-123. The capsule is preferably formed from methyl cellulose, polyvinyl alcohol or gelatin.

The capsule may also contain a reducing agent. Preferably the reducing agent sodium sulfite, sodium bisulfite or sodium thiosulfate. Especially preferred is sodium thiosulfate.

The pharmaceutical radioactive capsule may be filled by providing filler material supporting a pharmaceutically useful radioactive compound. Then transporting the filler material carrying the pharmaceutically useful radioactive compound into the chamber of the capsule. Also the filler material may support a reducing agent.

The filler material prior to being transported into the capsule chamber may be dissolved in a solvent or heated. Preferably the solvent is ethanol and the preferred temperature range for the heating method is 45° to 55° C.

One method of filling the capsules involves dispensing dissolved filler for example Carbowax (that is solid at room temperature) i.e. any of the polyethylene glycols from 1000 to 4000) in a solvent such as ethanol together with a reducing agent, preferably sodium thiosulfate in a solvent such as water, and the radioactive compound for example I-131 or I-123, into the capsules. Then removing the solvents by evaporation in a drying chamber but preferably in a temperature controlled vacuum dryer. Capsules made with this method maintained a radiochemical purity of above 99% for a period of 76 days. These capsules were impervious to degradation caused by a high humidity atmosphere (up to 75% relative humidity) over a period of 38 days.

Another method of making the capsule product of the present invention is to add a pharmaceutically useful radioactive compound to molten filler material. Then filling the capsules. An advantage of molten filler over solvent filler is that a drying cycle is not required. The molten filler solidifies as it cools within the capsule and therefore can be encapsulated with the top half immediately after filling. The solvent-filler preferably undergoes at least a 1 hour drying period in a temperature controlled vacuum drying chamber. Preferably, a base is provided in the heated filler. Where the pharmaceutically useful radioactive compound is iodine, heating may cause radioiodination of the filler. The presence of a base controls pH and minimizes any radioiodination. Since heat is not used in the solvent filler a base preferably would not be included therein.

In the carbowax radioactive iodine embodiments some peroxide may be present in the carbowax. The peroxide may react with the radioactive iodine to produce against iodine. To prevent this, reducing agents may be added. Preferred reducing agents are sodium sulfite, sodium bisulfite and sodium thiosulfate. Especially preferred is sodium thiosulfate.

A fundamental function of the filler material is to maintain the pharmaceutically useful compound separate from the inner wall of the capsule. When the pharmaceutically useful compound is in contact with the capsule wall the pharmaceutically useful compound may combine with the material of the capsule wall thus lowering the effective amount of pharmaceutically useful compound in the capsule.

In a preferred embodiment of the invention the filler material is supported by the inner surface of the capsule and the capsule has a central axis and the filler material extends radially across the central axis of the capsule. The filler material supports a major portion of the radioactive compound within the interior of the filler material so that the major portion of the radioactive compound does not contact the inner surface of the capsule. Preferably, a major portion of the volume within and defined by said inner surface of said capsule contains said filler material.

Preferably a major portion of the volume within and defined by the inner surface of the capsule contains the filler material.

Carbowax has been added to a preferred formulation to act as a support media for the Sodium Radioiodide, thus preventing its interaction with the gelatin of the capsule. One method of manufacture is automatic filling of the capsules with small volumes of an alcoholic-aqueous solution containing the formula excipients and selective removal of the mobile liquid from the capsules in a drying chamber using heat and vacuum.

Example 1 shows the raw material per batch of 1000 capsules of the invention. Examples 2–7 and 10 show formulations per capsule of the invention. Examples 8–10 are methods of making the capsules and are within the scope of the invention.

In the examples $\mu$Ci is micro curies; I-131 is radioactive iodine having an isotope weight of 131. Carbowax 4000 and 1000 are polyethylene glycols made by Union Carbide having average molecular weights of 4000 and 1000.

EXAMPLE 1

| | per 50.0 mCi Batch* |
|---|---|
| Sodium Radioiodide I-131 Concentrate Solution | 0.093 grams |
| Sodium Thiosulfate U.S.P. | 0.093 grams |
| Polyethylene Glycol, 1540 N.F. | 33.64 grams |
| Water for Injection | 15.9 ml. |
| Alcohol (Ethanol) U.S.P. | 84.1 ml. |
| Gelatin Capsules | 1000 |

*Smaller or larger batches may be manufactured by decreasing or increasing the raw materials proportionately.

EXAMPLE 2

| | Per Capsule |
|---|---|
| Sodium Radioiodide I-131 Concentrate Solution | 50 $\mu$Ci* |
| Sodium Thiosulfate U.S.P. | 0.093 mg |
| Polyethylene glycol, 1540 N.F. | 33.64 mg |
| Alcohol (Ethanol) U.S.P. | 0.084 ml** |
| Water for Injection | 0.016 ml** |
| Gelatin Capsule | 1 |

*Activity on date of Calibration. Higher or lower potencies may be made by increasing or decreasing the radioactivity respectively or allowing higher potencies to decay.
**Removed by evaporation prior to sealing the Capsule.

EXAMPLE 3

| | Per Capsule |
|---|---|
| Sodium Radioiodide I-131 | 50 $\mu$Ci |
| Carbowax 4000 | 0.09 (ml) |

-continued

| | Per Capsule |
|---|---|
| NaHSO$_3$ | 0.25 mg |

EXAMPLE 4

| | Per Capsule |
|---|---|
| Sodium Radioiodide I-131 | 50 $\mu$Ci |
| Carbowax 1540 | 10 mg |
| Na$_2$SO$_3$ | 0.1 mg |
| Ethanol | 0.1 ml |

EXAMPLE 5

| | Per Capsule |
|---|---|
| Sodium Radioiodide I-131 | 50 $\mu$Ci |
| Carbowax 1540 | 94 mg |
| NaHSO$_3$ | 0.02 mg |
| K$_2$HPO$_4$ | 0.176 mg |
| Water | 0.01 ml |

EXAMPLE 6

| | Per Capsule |
|---|---|
| Sodium Radioiodide I-131 | 50 $\mu$Ci |
| Carbowax 1540 | 40 mg |
| Ethanol | 0.1 ml |

EXAMPLE 7

| | Per Capsule |
|---|---|
| Sodium Radioiodide I-131 | 50 $\mu$Ci |
| Carbowax 4000 | 94 mg |
| K$_2$HPO$_4$ | 0.175 mg |
| Water | 0.01 ml |

EXAMPLE 8

A formulation used to fill the capsules is as follows:
90 ml of a 40% solution of Carbowax 1000 in ethanol.
5 ml of a 20% solution of Na$_2$S$_2$O$_3$.
5 ml of H$_2$O containing the I-131.

A volume of 0.1 ml of the above solution was dispensed into each capsule. A melt tray holding the capsules in a platter is placed in a Heat-Vacuum drying chamber. Heat is applied to the base of the chamber by circulating water constantly maintained at 70° C. through the base. The vacuum is brought down to 27″ of Hg by bleeding N$_2$ gas into the system.

A platter is dried for one hour to two hours under the above conditions.

The chromatograms resulting from a stability study show a single sharp peak throughout seventy-six days.

EXAMPLE 9

This procuedure is for making 100 ml of bulk filling solution using vacuum chambers as are known in the art. Larger or smaller volumes can be made by proportionating the ingredients.

Dissolve 0.292 grams of Sodium Thiosulfate, in Water for Injection and adjust the total volume to 50 mls. Liquify 40.0 grams of Carbowax 1540, in a suitable receptacle by warming at a temperature not to exceed 70° C. Remove from warming chamber and, while still liquid, add ethanol, up to 100 ml with stirring. Make final adjustment to 100 ml with the ethanol when room temperature has been reached. Mix well. As a first step mix 84.1 ml of the Ethanolic Carbowax Solution with 15.9 ml of the Sodium Thiosulfate Solution in a suitable container. All or part of the 15.9 ml of the Sodium Thiosulfate Solution may be used to transfer and wash the sodium radioiodide into the container. Alternatively, all or part of the combined solutions may be used to transfer and wash the sodium radioiodide into the container. Following the transfer into the bulk filling container, mix by stirring, then assay. If the assay is low by not more than 20%, sodium radioiodide can be added to adjust the radioconcentration. If the assay is too high, the ethanolic Carbowax 1540 solution can be combined with the Thiosulfate Solution in the same ratio stipulated above, and used to dilute the bulk solution. Fill up to 0.1 ml of the bulk filling solution into the body of Gelatin Capsules. Seal the vacuum chambers and apply full vacuum. Determine the maximum vacuum attainable at the time and record. It should be 27 inches minimum. Shut off the vacuum valve, allow the chambers to equilibrate to atmospheric conditions. Open the special chambers, place the plates containing the filled capsule bottoms on the polyethylene spacing rods, seal the chambers with the lids. Fully open $N_2$ bleed valve to chamber when fully open the vacuum. Gradually close the $N_2$ bleed valve until the vacuum gauge reading is 1 to 1.5 inches lower than the value obtained above. Dry the capsules for a period of at least one hour under the above conditions but not to exceed one hour and twenty minutes. Seal the capsules with the Capsule top.

EXAMPLE 10

A product of the following composition per capsule is made by the procedure below:

|  | Per Capsules |
| --- | --- |
| Sodium Radioiodide I-131 | 50 μCi |
| Sodium Thiosulfate Pentahydrate | 0.628 mg |
| Diphotassium Phosphate Anhydrous | 0.175 mg |
| Carbowax 4000 | 94.05 mg |
| Water for Injection | 10.45 mg |

First melt 54 g of Carbowax 4000 in a suitable glass container within a hot water bath. Then transfer to the dispenser reservoir preheated to 60° C. ±3° C. Dissolve 6.28 g of $Na_2S_2O_3.5H_2O$ up to 100 ml with a 0.1 M $K_2HPO_4$ solution. Use 6 ml of the thiosulfate/potassium phosphate solution to dilute and transfer the sodium radioiodide to the dispenser reservoir. Allow ½ hour for the solutions to completely mix by bubbling $N_2$ through the solutions. Dispense 0.1 ml (4 drops) into each bottom half of the gelatin capsules.

We claim:

1. An article of manufacture comprising, a pharmaceutical capsule formed essentially of a nontoxic, water soluble material adapted to being ingested and rapidly disintegrating on contact with fluids of the gastro-intestinal tract and a polyethylene glycol filler material having a pharmaceutically useful radioactive iodine and a reducing agent dispersed therein, said capsule having a central axis and an inner surface, said inner surface defining a volume within said capsule, said filler material being supported by said inner surface of said capsule, a major portion of said volume within said capsule containing said filler material, said filler material having a shape which is coextensive with the inner surface of said capsule, said filler material extending radially across the central axis of said capsule, said filler material containing a major portion of said radioactive iodine within the interior of said filler material, whereby said major portion of said radioactive compound does not contact said inner surface of said capsule.

2. The article of claim 1 wherein said radioactive iodine is iodine 131 or iodine 123.

3. The article of claim 1 wherein said capsule is methyl cellulose, polyvinyl alcohol or gelatin.

4. The article of claim 1 wherein said reducing agent is sodium thiosulfate, sodium sulfite or sodium bisulfite.

5. The article of claim 1 further comprising a base dispersed throughout said filler material, and said reducing agent is sodium thiosulfate, sodium sulfite or sodium bisulfite.

6. A method of filling a pharmaceutical capsule having an inner surface defining a volume within said capsule, said capsule being formed essentially of a nontoxic, water soluble material adapted to being ingested and rapidly disintegrating on contact with fluids in the gastrointestinal tract comprising providing a polyethylene glycol filler material having a pharmaceutically useful radioactive iodine and a reducing agent dispersed therein and transporting said filler material into said capsule, whereby a major portion of said volume within said capsule is filled with filler material.

7. The method of claim 6 wherein said filler material is heated prior to said transporting and said filler material further has a base dispersed therein.

8. The method of claim 7 wherein said filler is heated to 50° to 60° C. prior to said transporting, and said polyethylene glycol additionally has a base dispersed throughout said filler.

9. The method of claim 6 wherein said filler material is dissolved in a solvent prior to said transporting and both said filler material and said solvent are transported into said capsule.

10. The method of claim 9 further comprising removing said solvent from said capsule.

* * * * *

UNITED STATES PATENT AND TRADEMARK OFFICE
CERTIFICATE OF CORRECTION

PATENT NO. : 4,349,529

DATED : September 14, 1982

INVENTOR(S) : Nabil A. Morcos, et al.

It is certified that error appears in the above-identified patent and that said Letters Patent is hereby corrected as shown below:

Column 3, line 40, Example 1, delete "0.0983 grams" and add in its place -- 50.0 mCi --

Signed and Sealed this

First Day of March 1983

[SEAL]

Attest:

Attesting Officer

GERALD J. MOSSINGHOFF

Commissioner of Patents and Trademarks